(12) United States Patent
Sperling

(10) Patent No.: US 7,659,994 B2
(45) Date of Patent: Feb. 9, 2010

(54) APPARATUS FOR THE DETERMINATION OF SURFACE PROPERTIES

(75) Inventor: Uwe Sperling, Geretsried (DE)

(73) Assignee: BYK Gardner GmbH, Geretsried (DE)

(*) Notice: Subject to any disclaimer, the term of this patent is extended or adjusted under 35 U.S.C. 154(b) by 237 days.

(21) Appl. No.: 11/230,295

(22) Filed: Sep. 19, 2005

(65) Prior Publication Data
US 2007/0206195 A1    Sep. 6, 2007

(30) Foreign Application Priority Data
Dec. 3, 2004    (DE) ........................ 10 2004 058 408

(51) Int. Cl.
G01B 11/30    (2006.01)

(52) U.S. Cl. ........................ 356/600; 356/445

(58) Field of Classification Search ................ 356/600, 356/445–448, 237.1–237.5
See application file for complete search history.

(56) References Cited

U.S. PATENT DOCUMENTS

| | | | | |
|---|---|---|---|---|
| 3,999,864 A * | 12/1976 | Mutter | ........................ | 356/448 |
| 4,583,858 A * | 4/1986 | Lebling et al. | ............... | 356/402 |
| 4,677,298 A * | 6/1987 | Zelmanovic et al. | ..... | 250/341.8 |
| 4,704,121 A | 11/1987 | Moise | | |
| 5,401,977 A * | 3/1995 | Schwarz | ................. | 250/559.1 |
| 5,642,192 A * | 6/1997 | Gordon et al. | .............. | 356/328 |
| 5,754,283 A * | 5/1998 | Keane et al. | ................... | 356/73 |
| 5,991,046 A * | 11/1999 | Shakespeare et al. | ....... | 356/429 |
| 6,166,393 A * | 12/2000 | Paul et al. | .............. | 250/559.08 |
| 6,233,053 B1 * | 5/2001 | Preston et al. | .............. | 356/445 |
| 6,404,502 B2 * | 6/2002 | Preston et al. | .............. | 356/445 |
| 6,842,250 B2 | 1/2005 | Schwarz | | |
| 6,975,404 B2 | 12/2005 | Schwarz | | |
| 7,177,032 B2 * | 2/2007 | Lex | ........................... | 356/600 |
| 7,184,147 B2 * | 2/2007 | Sperling | ..................... | 356/445 |
| 2001/0033382 A1 * | 10/2001 | Preston et al. | ............. | 356/445 |
| 2003/0169421 A1 * | 9/2003 | Ehbets | ........................ | 356/328 |
| 2004/0239919 A1 * | 12/2004 | Schwarz | .................. | 356/237.2 |
| 2005/0254049 A1 * | 11/2005 | Zhao et al. | .................. | 356/369 |
| 2007/0153285 A1 * | 7/2007 | Elton et al. | ................. | 356/446 |

FOREIGN PATENT DOCUMENTS

| | | |
|---|---|---|
| JP | 62-217140 A | 9/1987 |
| JP | 2001-183304 A | 7/2001 |
| JP | 2001-296626 A | 10/2001 |
| JP | 2004-072551 A | 3/2004 |
| JP | 2003-042965 A | 9/2004 |
| JP | 2004-333494 A | 11/2004 |

* cited by examiner

Primary Examiner—Hoa Q Pham
(74) Attorney, Agent, or Firm—Greer, Burns & Crain, Ltd.

(57) ABSTRACT

A device for determining properties of surfaces having at least one first radiation device having at least one radiation source emitting radiation, having at least one first radiation detector having a first radiation detector element which captures at least a portion of the radiation emitted from the radiation device and subsequently diffused and/or reflected off a measuring surface and emits at least one measuring signal characteristic of the reflected/diffused radiation, and at least one second radiation detector having a second radiation detector element capturing a portion of the radiation from the radiation device and diffused/reflected off a measuring surface and outputs a measuring signal characteristic of the reflected and/or diffused radiation, and at least one filter device which is placeable both in the optical path between the radiation device and the first radiation detector and in the optical path between the radiation device and the second radiation detector.

22 Claims, 3 Drawing Sheets

APPARATUS FOR THE DETERMINATION OF SURFACE PROPERTIES

BACKGROUND

The present invention relates to a device for determining the properties of surfaces.

The optical impression of objects or their surfaces, in particular the surfaces of motor vehicles, is decisively determined by their surface properties. Since the capability of the human eye to objectively evaluate surface properties is limited, there is a need of auxiliaries and equipment for qualitatively and quantitatively determining the properties of surfaces.

The properties of surfaces determined are for example gloss, orange peel, color, macro- and/or micro texture, distinctness of image, haze, surface texture and/or topography, and the like.

Devices are known from the prior art in which a radiation means projects radiation onto the examined measuring surface and the radiation reflected and/or diffused off said measuring surface is captured and evaluated by a detector. Many applications require or prefer that an examination of the reflected radiation includes the color or the individual spectral components.

To this end the prior art has used filters positioned in the optical path between the radiation means and the radiation detector. On the other hand it is also preferred in the prior art to measure under different angles the radiation reflected off the measured surface. In this case a plurality of detectors is applied.

For this reason the prior art places several filter means in the individual optical paths between the radiation means and various radiation detectors. It is known to provide one or more filters in every optical path.

On the one hand this will raise the costs for such devices since a large number of filters must always be installed. On the other hand these configurations may also reduce precision since although specified for the same wavelengths filters do not always accurately comprise identical optical properties such that equal filters may still lead to unequal measured results.

SUMMARY OF THE INVENTION

It is therefore an object of the present invention to provide a device for determining surface properties which keeps the costs for the filters and thus the overall costs low. Also, the precision of the corresponding devices is intended to be improved.

This object of the invention is achieved by a device according to claim 1. Preferred embodiments and more specific embodiments are the objects of the subclaims. However, reference is made to the fact that all the objects are not necessarily achieved to the same extent by all the objects of all the subclaims.

The device of the present invention for determining the properties of surfaces comprises at least one first radiation means having at least one radiation source which emits radiation. In addition, at least one first radiation detection means having a first radiation detector element is provided which captures at least a portion of the radiation emitted from said at least one radiation means and subsequently reflected off a measuring surface and which outputs at least one measurement signal which is characteristic of the reflected and/or diffused radiation. Furthermore at least one second radiation detection means having a second radiation detector element is provided which captures at least a portion of the radiation emitted from said at least one radiation means and subsequently reflected off the measuring surface and which outputs at least one measurement signal which is characteristic of the reflected and/or diffused radiation. Furthermore at least one filter means is provided which can be placed both in the optical path between the radiation means and the first radiation detector element and in the optical path between the radiation means and the second radiation detector element.

The device of the invention allows to use one filter means for one or more radiation detection means.

A measuring surface is understood to mean the surface which returns, in particular reflects and/or diffuses, at least a portion of the radiation incident thereon. Measuring surfaces within the scope of the present invention are in particular understood to mean the surfaces of motor vehicles such as in particular but not exclusively their coated surfaces. Measuring surfaces may additionally include the surfaces of furniture and the like.

In another preferred embodiment at least one first radiation means comprises at least one radiation source selected from a group of radiation sources comprising thermal radiation sources such as in particular but not exclusively light bulbs, halogen light bulbs, coherent and non-coherent semiconductor radiation sources, gas discharge radiation sources, lasers and the like. The emitted radiation is preferably, but not exclusively, light in the visible spectrum. However, light in the infrared and/or ultraviolet spectral ranges may also be used. The preferred radiation sources used are light-emitting diodes (LEDs).

Preferably the radiation source emits standard light such as in particular but not exclusively A, B, C, D50, D65, D11 or TL84 standard light. It is particularly preferred that the radiation source emits D65 standard light.

Using standard light and in particular using the reference light type D65 will enhance the determination of easily comparable surface variables. The reference light type D65 is representative of a phase of natural daylight at the color temperature of 6500 Kelvin. The, precise theoretical emission spectrum of D65 standard light is preferably approximated by means of xenon lamps.

A radiation means preferably comprises several radiation sources whose radiation characteristics are particularly preferably different, at least partially. In a particularly preferred embodiment at least one radiation means comprises a plurality of radiation sources having different radiation characteristics wherein it is particularly preferred that substantially the entire visible wavelength range and the individual radiation sources are covered.

A filter means is understood to mean a device that comprises different optical properties for different components of light transmitting through or reflected off it, in particular but not exclusively for different spectral ranges. In a preferred embodiment these are spectral filters allowing individual wavelength ranges to be transmitted while being opaque to other ranges.

In another preferred embodiment at least one radiation detector element allows the spatially resolved detection of radiation. Said radiation detector element is preferably a detector element comprising a CCD chip or the like. In another preferred embodiment the second radiation detector element also allows the spatially resolved detection. Preferably several radiation detector elements are provided all of which allow the spatially resolved detection of radiation. The spatially resolved detection is understood to mean that not only a mean value is output for the examined parameters such as the intensity, but the value of said measured variable is output in dependence on the locus on the surface of the detector which receives the radiation.

In another preferred embodiment the device comprises a plurality of radiation detector elements wherein at least one filter means can be placed in the optical paths between the radiation means and each of said radiation detector elements.

Another preferred embodiment provides a plurality of filter means. These different filter means preferably serve to analyze different spectral wavelength ranges, i.e. each does or does not transmit specific spectral wavelength ranges.

Preferably each filter means from the plurality of filter means can be placed in the optical paths between the radiation means and at least two radiation detector elements. Preferably each filter means from the plurality of filter means can be placed in all of the optical paths between the radiation means and all of the radiation detector elements.

In this way one set of filters can simultaneously be used for filtering in all of the radiation detector elements, which is thus a particularly efficient configuration of the device of the invention.

In another preferred embodiment the plurality of filter means is positioned on a shared carrier means. In this way it can be ensured that the individual filter means are guided in a predefined way into the respective optical paths between the radiation means and the individual radiation detector elements. A carrier means is understood to mean any means suitable to position the individual filter means in predefined configurations or in particular to guide them relative to the optical paths.

It is preferred that at least two filter means exhibit different optical properties. As illustrated above, filter means are provided whose optical properties differ from one another. Preferably it is also conceivable to provide individual filters having equal filtering properties so as to achieve that similar filter means sit in specific places on the carrier means in two or more optical paths.

In another preferred embodiment the filter means can be placed in an optical path between the measuring surface and the radiation detector element. In this way it is achieved that the optical paths are filtered separately. Contrary to this a filter means placed in an optical path between the radiation means and the measuring surface would affect the incident light on the measuring surface substantially uniformly.

Another preferred embodiment provides that at a specified moment, filter means having different optical properties can be placed in the optical paths between the radiation means and at least two radiation detector elements. This means that as a filter means is guided into one optical path, another filter means will simultaneously be guided into another optical path between the radiation means and another corresponding radiation detector element.

In another preferred embodiment the filter means placed on the carrier means can travel in respect of the optical paths between the radiation means and the radiation detector elements. This means that the individual filter means can be pushed through two or more individual optical paths. The number of filter means positioned on the carrier means is preferably between 2 and 50, preferably between 10 and 40 and particularly preferably between 20 and 30. It is preferred to provide filter means which are equal relative to one another such that the number of filter means illustrated herein increases on the whole.

In another preferred embodiment the carrier means is deformable at least in portions. In another preferred embodiment the filter means themselves may also be deformable at least in portions such that they can be placed in different positions.

In another preferred embodiment the carrier means is transported on at least one roller at least in portions. Preferably a plurality of rollers is provided by means of which the carrier means can be placed in the optical paths between the individual radiation detector elements and the measuring surface. In one embodiment, the carrier means is a belt that is flexible at least in portions on which the individual filter means are positioned. According to the present invention the carrier means is considered to be flexible if it comprises two or more rigid members which are movable relative to one another. Preferably the respective filter means can be positioned on the individual rigid members.

In another preferred embodiment at least one radiation deflection means is positioned in the optical path between the measuring surface and at least one detector element. Said radiation deflection means serves to deflect the beam reflected off the measuring surface in such a way that the individual radiation detector elements can be placed in preferred positions relative to one another for example on the same plane.

In another preferred embodiment the spatial position of at least one radiation deflection means is variable. This allows adjustment to take place such that the individual beams reflected off the measuring surface can be arranged in a preferred configuration relative to one another such as on one plane.

The invention is further directed at a device for determining the properties of surfaces comprising at least one first radiation means having at least one radiation source emitting radiation, and at least one second radiation means having at least one radiation source emitting radiation. In addition, at least one first radiation detection means having at least one radiation detector element is provided which captures at least a portion of the radiation emitted from said radiation means and subsequently reflected off said measuring surface and which outputs at least one measurement signal which is characteristic of the reflected and/or diffused radiation. According to the invention at least one filter means is furthermore provided which can be placed both in an optical path between the first radiation means and the radiation detector element, and in an optical path between the second radiation means and the radiation detector element.

Preferably the radiation detector element allows the spatially resolved detection of radiation. In another preferred embodiment the filter means can be placed in the optical path between the individual radiation means and the measuring surface.

In another preferred embodiment each one filter means from a plurality of filter means can be placed in the optical paths between each radiation means and the radiation detector. element.

Compared to the embodiments mentioned above, these embodiments specified and the embodiments following below are based on the same inventive concept having as its object to economize on filter means and also to improve measuring to be more reliable on the whole. For this reason the preferred embodiments illustrated above can be applied to both basic configurations, i.e. the embodiment comprising one radiation means and several radiation detector elements and the other embodiment comprising several radiation means and one radiation detector element. A more specific illustration of the embodiments already illustrated is therefore omitted.

Preferably each filter means from the plurality of filter means can be placed in the optical paths between at least two radiation means and the radiation detector element. Preferably the filter means can be placed in an optical path between the radiation means and the measuring surface. This embodiment is a corresponding specific embodiment of the above embodiment where one radiation means and several radiation detector elements are provided and the filter means is positioned between measuring surface and radiation detector element.

Another preferred embodiment provides that at a specified moment, filter means having different optical properties can be placed in the optical paths between at least two radiation means and the radiation detector element. This allows to simultaneously evaluate different spectral radiation components at different locations and thus at different angles.

A radiation deflection means is preferably positioned in the optical path between at least one radiation means and the measuring surface. As in the above embodiments said radiation deflection means may be mirrors, prisms or the like. Radiation deflection means are preferably placed in several optical paths between the radiation means and the measuring surface.

In another preferred embodiment the spatial position of at least one radiation deflection means is variable. This means that the angle at which the radiation is incident on the mirror and thus the angle at which the radiation is deflected, is variable.

In another preferred embodiment, a combination of the two basic concepts mentioned above may be used, meaning several radiation detector elements and several radiation means. In this way the individual filters may be placed both in the optical path in front of the measuring surface and behind the measuring surface.

The specific embodiments described above can be applied to such a combination.

The present invention is also directed at a method for determining the properties of surfaces where radiation is emitted at a predetermined solid angle to an examined surface, the radiation emitted to and reflected back from said measuring surface is detected by means of at least one first and one second radiation detector element and furthermore at least one filter means is guided both through the optical path between the radiation means and the first radiation detector element and through the optical path between the radiation means and the second radiation detector element.

In another method according to the invention radiation is emitted to an examined measuring surface from a first radiation means at a first predefined solid angle and from a second radiation means at a second predefined solid angle. In another method the radiation emitted to and reflected back from the measuring surface is detected by means of a radiation detection means comprising a radiation detector element. In another method step at least one filter means is guided both through the optical path between the first radiation means and the radiation detector element and through the optical path between the second radiation means and the radiation detector element.

BRIEF DESCRIPTION OF THE DRAWINGS

Other advantages and embodiments can be taken from the accompanying drawings. These show in.

DETAILED DESCRIPTION OF THE PREFERRED EMBODIMENT

Figure 1:
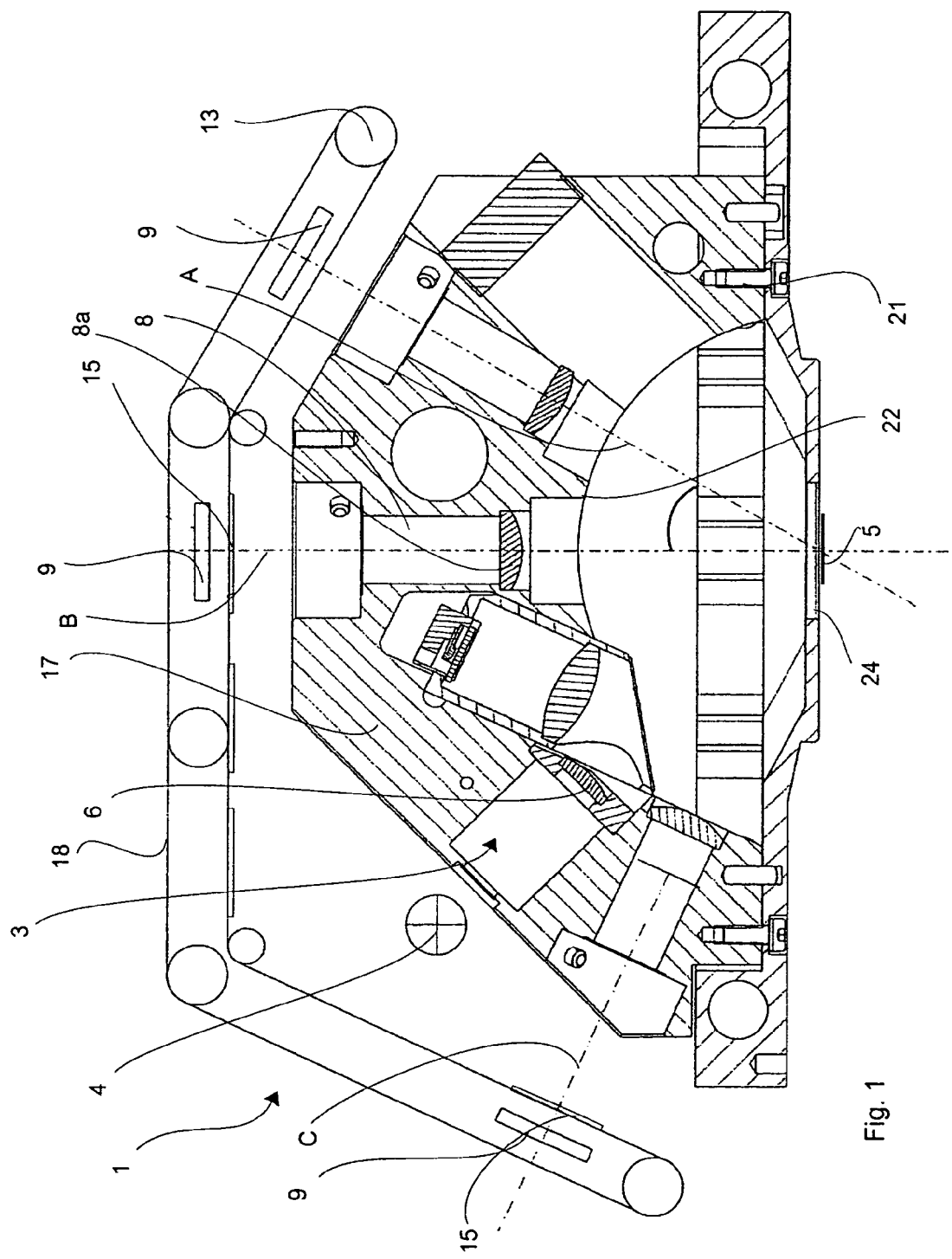
FIG. 1 is a vertical section of the present device for examining the properties of surfaces in a first embodiment.

FIG. 1 shows the device 1 of the invention for determining the properties of surfaces. It comprises a radiation means 3 comprising a radiation source 4 and an optical illumination system 6. Preferably said system is a lens or a lens system. The light, originating from the radiation means 3, is projected through an aperture 24 to the examined surface 5. The light returning from, in particular diffused and/or reflected off the examined surface 5 is detected by detection means 8 at several predefined angles $\alpha_1$, $\alpha_2$. Said detection means preferably also comprise optical means 8a and detector elements 9. In this embodiment said detector elements 9 perform the spatially resolved detection of incident radiation. Preferably the optical system 8a forms an image on the detector element 9.

The optical paths A, B between the measuring surface 5 and the individual detector elements 9 can receive filter means 15. In this embodiment said filter means exhibit different optical properties such as different spectral transmission ranges. The individual filter means 15 are positioned on a belt 18 that travels around various guide rollers 13. The embodiment illustrated in FIG. 1 has front rollers and rear rollers hidden by said front rollers. The individual filter means 15 are guided between said rollers.

Another embodiment also allows the individual filter means 15 to be directly or indirectly hinge-jointed so as to travel chain-like around the individual guide rollers 13.

The embodiment shown in FIG. I has filter means that are preferably configured such that one filter means 15 each will simultaneously be positioned in the optical paths A, B between the measuring surface and the individual detector elements 9. The filter means may also be configured such that at least in specified positions, one filter means will be positioned in all of the optical paths mentioned, or that in other specified positions at least in several optical paths, filter means having substantially identical optical properties will be positioned.

According to one method of the invention, the belt carrying the individual filters is guided into the individual optical paths A, B and C, and measurement takes place one by one using different filters. In this way it is possible to perform measurements at the different angles related to the optical paths A, B and C, using different optical filter means.

The reference numeral 22 refers to an inner surface of the measuring space which is preferably configured to be absorbing.

A corresponding alternative (not shown) may provide instead of the one radiation means 3, a plurality of radiation means and instead of the plurality of radiation detector elements, only one radiation detector element 9. In this case the filter means 15 or the belt will preferably extend between the individual radiation sources 4 and the aperture 24 or the measuring surface 25. As mentioned above, light is incident in this embodiment at different angles and is detected in one direction or at one angle. Also in this embodiment it is preferred to use a radiation detector element which allows the spatially resolved detection of radiation.

Figure 2:
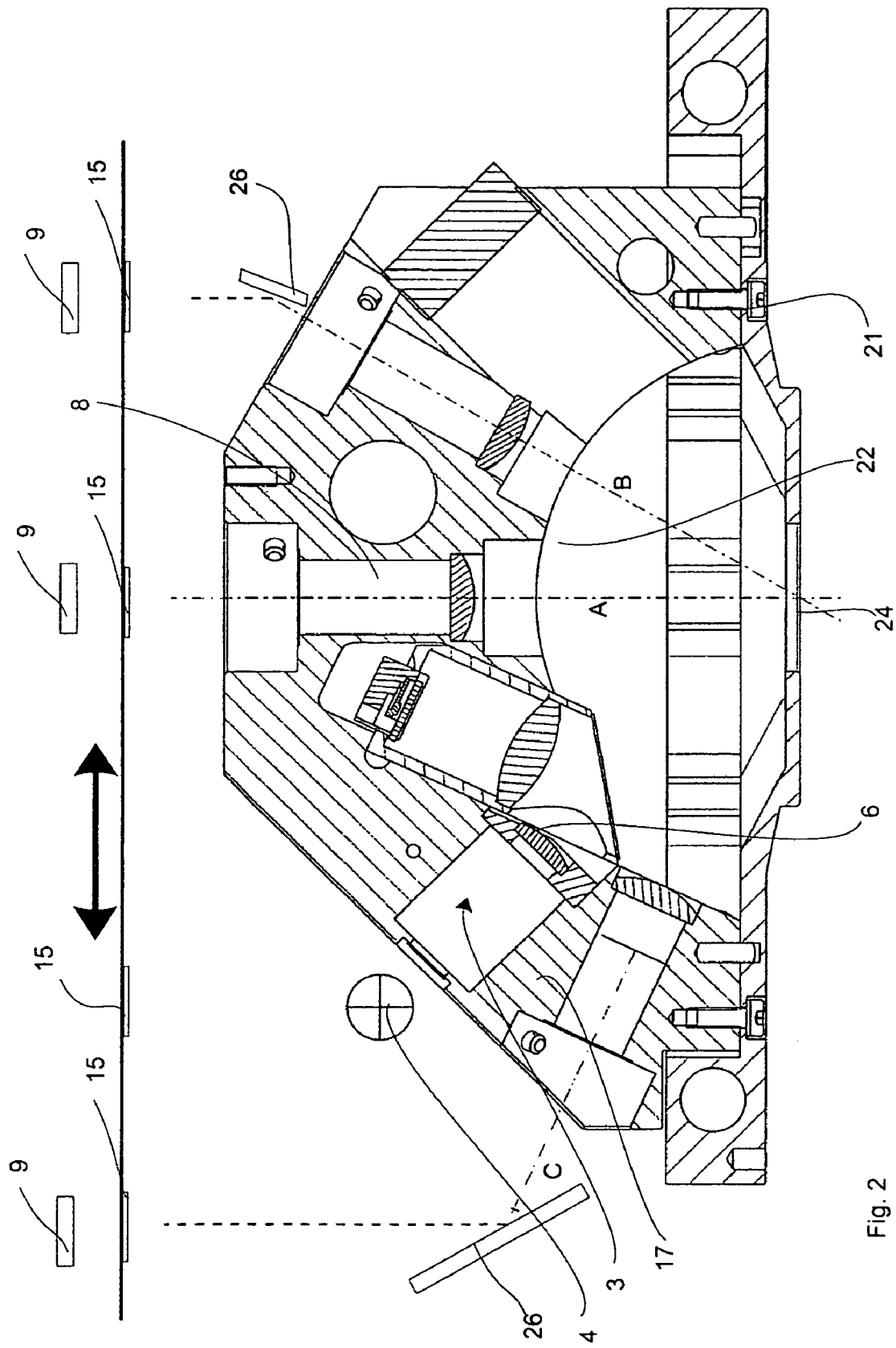
FIG. 2 is a vertical section of the present device for examining the properties of surfaces in a second embodiment.

FIG. 2 shows another embodiment of the device of the invention for determining the properties of surfaces. Unlike the embodiment shown in FIG. 1, the individual filter means 15 are positioned on a substantially horizontal carrier means. This embodiment has the advantage that the carrier means does not need to be guided over rollers and is thus not bent nor deformed. For bringing the individual radiation components reflected off the measuring surface 25 onto the same plane which substantially coincides with or is parallel to the plane where the carrier means 18 is positioned, deflection mirrors 26 are applied. Said deflection mirrors comprise adjusting means (not shown) for imaging the radiation reflected off the surface on the respective detector elements 9.

In the same way as in the embodiment shown in FIG. 1, the individual filter means are pushed into the optical path between the measuring surface and the respective detector element 9. In this embodiment the filter means are also positioned such that at specified moments or in specified positions on the carrier means a filter means will be positioned in all of the optical paths A, B, C. Furthermore, constellations are conceivable where no filter means is provided in one or more optical paths while filter means are provided in other optical paths.

This embodiment may be applied correspondingly to devices comprising a plurality of radiation means and one radiation detector element. In this case the individual filter means will be positioned between the radiation sources and the measuring surface 25.

Figure 3:
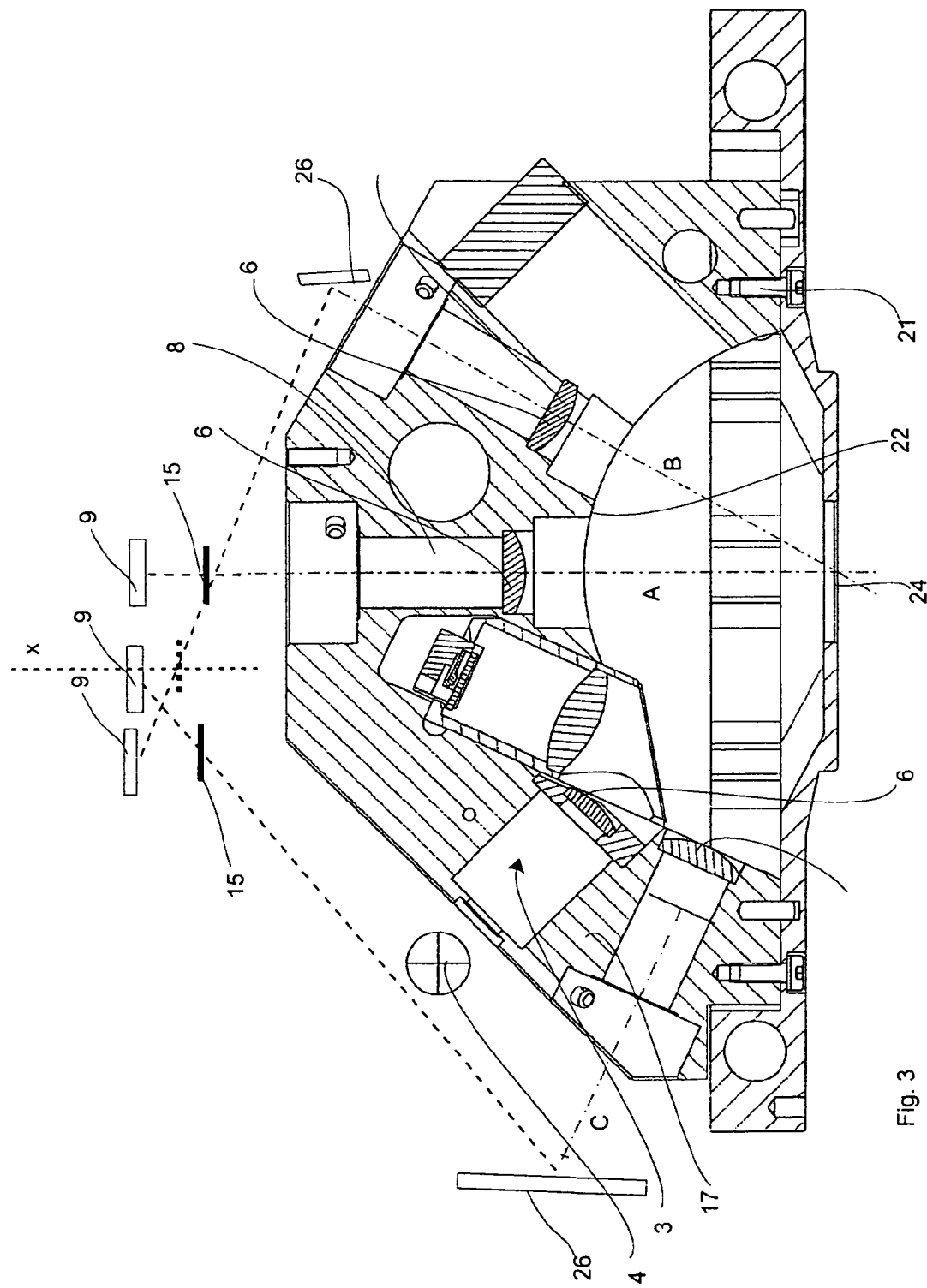
FIG. 3 is a vertical section of the present device for examining the properties of surfaces in another embodiment.

FIG. 3 shows another embodiment of the device of the invention for determining the properties of surfaces. Also in this case, deflection mirrors 26 are provided for deflecting the light reflected off the measuring surface 25 toward radiation detector elements 9. This embodiment provides that the radiation detector elements are not only positioned on one plane but also on an annular portion. In this case the plurality of filter means 15 is positioned on a carrier means that is annular at least in portions. It rotates about an axis x such that in this case the individual filter means 15 can also be guided into the optical paths A, B and C.

This embodiment may also, as above, provide the reverse case with a plurality of radiation means and one radiation detector element wherein the filter means will be positioned between the radiation means and the measuring surfaces.

The invention claimed is:

1. A device for determining the properties of surfaces comprising:
at least one first radiation means having at least one radiation source which emits radiation;
at least one first radiation detection means having a first radiation detector element which captures at least a portion of the radiation emitted from the at least one radiation means and subsequently diffused and/or reflected off a measuring surface and outputs at least one measuring signal which is characteristic of the reflected and/or diffused radiation;
at least one second radiation detection means having a second radiation detector element which captures at least a portion of the radiation emitted from the at least one radiation means and subsequently diffused and/or reflected off the measuring surface and outputs at least one measuring signal which is characteristic of the reflected and/or diffused radiation; and
at least one travelling filter means wherein the same traveling filter means is selectively positionable in an optical path between the measuring surface and the first radiation detector element as well as in an optical path between the measuring surface and the second radiation detector element, said respective optical paths being displaced from each other.

2. The device according to claim 1, wherein said at least one filter means can be placed in the optical paths between the measuring surface and each radiation detector element.

3. The device according to claim 1, wherein a plurality of said at least one filter means is provided and each filter means from a plurality of filter means can be placed in the optical paths between the measuring surface and at least two radiation detector elements.

4. The device according to claim 1, wherein said at least one filter means can be placed in the optical path between the measuring surface and an arbitrary radiation detector element.

5. The device according to claim 1, wherein at a specified moment, said at least one filter means having different optical properties can be placed in the optical paths between the measuring surface and at least two radiation detector elements.

6. The device according to claim 1, further comprising at least one radiation deflection means arranged in the optical path between the measuring surface and at least one radiation detector element.

7. The device according to claim 6, wherein a spatial position of said at least one radiation deflection means is variable.

8. The device according to claim 1, wherein said at least one radiation detector means is a detector element that allows the spatially resolved detection of radiation.

9. A device for determining the properties of surfaces comprising:
at least one first radiation means having at least one radiation source emitting radiation at a measuring surface;
at least one second radiation means having at least one radiation source emitting radiation at the measuring surface, said at least one first and second radiation means being arranged at different angles relative to the measuring surface;
at least one first radiation detection means having a radiation detector element which captures at least a portion of the radiation emitted from the radiation means and subsequently diffused and/or reflected off the measuring surface and outputs at least one measuring signal which is characteristic of the reflected and/or diffused radiation;
at least one travelling filter means wherein the same traveling filter means can be placed for or during measurement in an optical path between the first radiation means and the radiation detector element and as well as in an optical path between the second radiation means and the radiation detector element; and
a plurality of said at least one travelling filter means are arranged on a shared carrier means.

10. The device according to claim 9, wherein said at least one filter means can be placed in the optical paths between each said radiation means and an arbitrary radiation detector element.

11. The device according to claim 9, wherein a plurality of said at least one filter means is provided and each filter means from the plurality of filter means can be placed in the optical paths between at least two radiation means and at least said radiation detector element.

12. The device according to claim 9, wherein said at least one filter means can be placed in the optical path between the radiation means and the measuring surface.

13. The device according to claim 9, wherein at a specified moment, said at least one filter means having different optical properties can be placed in the optical paths between at least two radiation means and the radiation detector element.

14. The device according to claim 9, further comprising at least one radiation deflection means arranged in the optical path between at least one radiation means and the measuring surface.

15. The device according to claim 14, wherein a spatial position of said at least one radiation deflection means is variable.

16. The device according to claim 9, wherein a plurality of said radiation detector elements is provided.

17. The device according to claim 9, wherein at least two said at least one filter means exhibit different optical properties.

18. The device according to claim 9, wherein the number of said at least one filter means arranged on a carrier means is between 2 and 50, between 10 and 40 or between 20 and 30.

19. The device according to claim 9, wherein said carrier means is deformable at least in portions.

20. The device according to claim 9, wherein said carrier means is transported on at least one roller at least in portions.

21. A method for determining the properties of surfaces including the steps:

emitting radiation onto an examined measuring surface at a specified solid angle;

detecting the radiation emitted to and reflected and/or diffused off the measuring surface by means of at least one first and at least one second radiation detector element;

placing at least one travelling filter means wherein the same traveling filter means is placed at a first specified moment for or during measurement in an optical path between the measuring surface and the first radiation detector element as well as at a second specified moment for or during measurement in an optical path between the measuring surface and the second radiation detector element, said respective optical paths being displaced from each other.

22. The method of claim 21, wherein said first specified moment and the second specified moment occur at different times.

* * * * *